United States Patent
Rao et al.

(10) Patent No.: US 9,801,609 B2
(45) Date of Patent: Oct. 31, 2017

(54) DEVICE AND METHOD FOR ENHANCING ACCURACY OF RECOGNIZING FETUS HEART RATE ACCELERATION DATA

(71) Applicant: EDAN INSTRUMENTS, INC., Nanshan, Shenzhen (CN)

(72) Inventors: Jian Rao, Shenzhen (CN); Dewei Chen, Shenzhen (CN); Yonghua Zeng, Shenzhen (CN); Wusun Chen, Shenzhen (CN)

(73) Assignee: EDAN INSTRUMENTS INC., Shenzhen (CN)

( * ) Notice: Subject to any disclaimer, the term of this patent is extended or adjusted under 35 U.S.C. 154(b) by 948 days.

(21) Appl. No.: 14/235,050

(22) PCT Filed: Sep. 25, 2012

(86) PCT No.: PCT/CN2012/081934
§ 371 (c)(1),
(2) Date: Jan. 25, 2014

(87) PCT Pub. No.: WO2013/013646
PCT Pub. Date: Jan. 31, 2013

(65) Prior Publication Data
US 2016/0310102 A1    Oct. 27, 2016

(30) Foreign Application Priority Data
Jul. 26, 2011   (CN) .......................... 2011 1 0209521

(51) Int. Cl.
*A61B 8/08*     (2006.01)
*A61B 8/02*     (2006.01)
*A61B 5/024*    (2006.01)
*A61B 5/00*     (2006.01)

(52) U.S. Cl.
CPC ........ *A61B 8/0866* (2013.01); *A61B 5/02411* (2013.01); *A61B 5/7235* (2013.01);
(Continued)

(58) Field of Classification Search
CPC ....................... A61B 5/024–5/02411
See application file for complete search history.

(56) References Cited

U.S. PATENT DOCUMENTS

2004/0133115 A1   7/2004   Hamilton
2006/0229518 A1   10/2006  Ofek
(Continued)

FOREIGN PATENT DOCUMENTS

CN    1323012 A    11/2001
CN    1942135 A    4/2007
(Continued)

OTHER PUBLICATIONS

International Search Report, dated Jan. 31, 2013.

*Primary Examiner* — Serkan Akar
(74) *Attorney, Agent, or Firm* — Symbus Law Group, LLC; Clifford D. Hyra (57) ABSTRACT

The present invention relates to the field of biomedical signal processing, specifically, a device and method of implementation for enhancing the accuracy of fetal heart rate acceleration data recognition. The present invention comprises: collecting fetal heart rate data in a pre-configured period so as to obtain a fetal heart rate data sequence, H(n); performing baseline identification on the fetal heart rate sequence, H(n), to obtain a fetal heart rate baseline data sequence, B(n); pre-processing the fetal heart rate data sequence, H(n), to obtain a pre-processed fetal heart rate data sequence, C(n); performing acceleration recognition on the pre-processed fetal heart rate data sequence, C(n), according to pre-configured acceleration determination criteria and the fetal heart rate baseline data sequence, B(n), to obtain acceleration data segments; calculating an acceleration attribute value for each of the acceleration data segments, and outputting each acceleration data segment and the acceleration attribute value calculation result thereof.

(Continued)

The technical solution provided by the present invention effectively distinguishes the variations between the accelerations and the baseline, accurately recognizes each acceleration in continuous accelerations, and avoids the situations of the detected number of fetal heart rate data accelerations being lower than the actual number or being mistaken due to current methods, thereby enhancing the accuracy in recognizing fetal heart rate curve accelerations.

13 Claims, 6 Drawing Sheets (52) U.S. Cl.
CPC ............. *A61B 8/02* (2013.01); *A61B 8/5207* (2013.01); *A61B 8/5223* (2013.01); *A61B 8/5276* (2013.01)

(56) References Cited

U.S. PATENT DOCUMENTS

| | | | |
|---|---|---|---|
| 2008/0045849 A1* | 2/2008 | Outram | A61B 5/02411 600/508 |
| 2009/0054797 A1 | 2/2009 | Miller | |
| 2010/0274145 A1* | 10/2010 | Tupin, Jr. | A61B 5/0444 600/511 |

FOREIGN PATENT DOCUMENTS

| | | |
|---|---|---|
| CN | 102048534 A | 5/2011 |
| CN | 102048558 A | 5/2011 |
| CN | 102210586 A | 10/2011 |
| CN | 102302363 A | 1/2012 |
| GB | 2471667 A | 1/2011 |

\* cited by examiner

DEVICE AND METHOD FOR ENHANCING ACCURACY OF RECOGNIZING FETUS HEART RATE ACCELERATION DATA

This application claims the benefit of Chinese patent application No. 201110209521.4, filed Jul. 26, 2011, which is hereby incorporated by reference in its entirety.

FIELD OF THE INVENTION

The invention relates to the field of biomedical signal processing and specifically to a device for enhancing the accuracy of recognizing fetal heart rate acceleration and a realizing method thereof.

BACKGROUND OF THE INVENTION

The fetal heart rate acceleration is a unique physiological phenomenon in the third trimester and also an important indicator used for determining the fetal safety in the uterus in clinical practice. During pregnancy, if the fetal heart rate acceleration occurs because of fetal movement, external stimuli, etc., the phenomenon shows that fetal is healthy. In the delivery period, the fetal heart rate acceleration is one of the important indicators that the fetus is well stockpiled. If the uterus has recurrent contraction and periodic acceleration, it indicates that the cord has mild compression. In this case, its changes shall be observed to determine whether the necessary interventions shall be taken to ensure fetal safety. Conversely, the fetal heart rate lacking acceleration for a long time is a sign of fetal hypoxia. At this time, the appropriate clinical trials shall be taken to determine the fetal situation and take corresponding interventions.

Clinically, the following criteria are generally taken to judge and process fetal heart rate data acceleration: when gestational weeks are equal to or greater than 32 weeks, it is determined to be in acceleration if the fetal heart rate suddenly increases to be above the fetal heart rate baseline. An acceleration is a visually apparent abrupt increase in fetal heart rate. An abrupt increase is defined as an increase from the onset of acceleration to the peak in less than 30 seconds. To be called an acceleration, the peak must be equal to or greater than 15 bpm, and the acceleration must last 15 seconds or longer from the onset to return. Before 32 weeks of gestation, acceleration is defined as having a peak equal to or greater than 10 bpm and a duration equal to or more than 10 seconds from the onset to return.

Currently, in the field of the prior art, the intermediate data processing method of the automatic recognition of fetal heart rate is mainly based on the acceleration medical criteria. Firstly, with a fetal monitoring module, fetal heart rate is collected and fetal heart rate baseline is recognized. Then, according to pre-configured medical criteria, the number, duration, amplitude, etc. of the acceleration above the baseline are calculated. However, in practice, if the acceleration is recognized only based on the acceleration medical criteria, the method has the following disadvantages: firstly, when a fetal is active or in continuous stimulation, the collected data often have continuous acceleration. That is, when the last acceleration is completed but the curve of the fetal heart rate is not yet returned to the baseline, the next acceleration starts. With the method, the continuous accelerations are only recognized as one acceleration but not recognized as a plurality of accelerations. Hence, the number of the recognized accelerations is less than the actual number of the accelerations. Secondly, the curve of the fetal heart rate data often comprises the variation part of the baseline. The method may not recognize the variation part of the baseline and hence exclude them from the acceleration. Moreover, the variation part of the baseline often meets the above criteria but does not belong to the acceleration. If the acceleration is determined according to the method, the variation part of these baselines is mistakenly regarded as the acceleration.

SUMMARY OF THE INVENTION

In order to overcome the abovementioned disadvantages, the objective of the invention is to propose a device and method for enhancing the accuracy of recognizing fetal heart rate data acceleration.

The objective is realized through the following technical proposals:

The invention is a device and method for enhancing accuracy of recognizing fetal heart rate acceleration, wherein a device for enhancing the accuracy of recognizing fetal heart rate acceleration mainly comprises a fetal heart rate data collecting module, a fetal heart rate data baseline recognition module, a fetal heart rate data preprocessing module, a fetal heart rate data acceleration recognition module and an output module;

the fetal heart rate data collecting module is used for performing the fetal heart rate data collection in a pre-configured period to obtain a fetal heart rate data sequence, H(n);

the fetal heart rate data baseline recognition module is connected with the fetal heart rate data collecting module to be used for receiving the fetal heart rate data sequence, H(n), transmitted by the fetal heart rate data collecting module and recognizing a fetal heart rate baseline sequence, B(n);

the fetal heart rate data preprocessing module is connected with the fetal heart rate data collecting module to be used for receiving the fetal heart rate data sequence, H(n, transmitted by the fetal heart rate data collecting module and performing preprocessing on the sequence H(n) to obtain a fetal heart rate data sequence, V(n);

the fetal heart rate data acceleration recognition module is connected with the fetal heart rate data baseline recognition module and the fetal heart rate data preprocessing module to be used for receiving the fetal heart rate baseline sequence, B(n), transmitted by the fetal heart rate data baseline recognition module and the preprocessed sequence, V(n), transmitted by the fetal heart rate data preprocessing module; the acceleration recognition on the preprocessed fetal heart rate data sequence V(n) is performed to obtain an acceleration data segment, according to a pre-configured acceleration determination criteria and the fetal heart rate data baseline sequence, B(n), and the output module is connected with the fetal heart rate data acceleration recognition module to be used for receiving the acceleration data segment transmitted by the fetal heart rate data acceleration recognition module and outputting it.

As the further technical proposal of the invention, the device for enhancing the accuracy of recognizing fetal heart rate acceleration also comprises a fetal heart rate signal collecting and processing transforming module, a fetal heart rate data acceleration validation module, a fetal heart rate data acceleration determination criteria setting module, a fetal heart rate data acceleration type determination module, a collecting duration setting and determination module and a fetal heart rate data acceleration attribute calculation module, wherein the fetal heart rate signal collecting and processing transforming module is connected with the fetal heart rate data collecting module to be used for collecting a fetal heart signal, transforming the signal into the fetal heart rate data and transmitting the fetal heart rate data to the fetal heart rate data collecting module;

the fetal heart rate acceleration validation module is connected with the fetal heart rate data acceleration recognition module and the fetal heart rate data acceleration attribute calculation module to be used for receiving the acceleration data segment transmitted by the fetal heart rate data acceleration recognition module; according to the signal loss condition of each acceleration, the fetal heart rate data acceleration validation module validates whether each acceleration sequence segment is in real acceleration, and transmits the validation result to the fetal heart rate data acceleration attribute calculation module;

the fetal heart rate data acceleration determination criteria setting module is connected with the fetal heart rate acceleration recognition module to be used for setting the fetal heart rate data acceleration determination criteria in advance and transmitting the determination criteria to the fetal heart rate data acceleration recognition module;

the fetal heart rate data acceleration type determination module is connected with the fetal heart rate data acceleration attribute calculation module to be used for determining the acceleration type under the conditions of simultaneously collecting uterine contraction data and transmitting the determination result to the fetal heart rate data acceleration calculation module;

the collecting duration setting and determination module is connected with the fetal heart rate data collecting module and used for setting the collecting duration of the fetal heart rate data, and determining whether the collected data time exceeds the set duration. If it exceeds the set duration, a timeout signal is transmitted to the fetal heart rate data collecting module; and the fetal heart rate data acceleration attribute calculation module is connected with the fetal heart rate data acceleration recognition module and the output module to be used for receiving the acceleration data segment transmitted by the fetal heart rate data acceleration recognition module, calculating the duration, amplitude and other acceleration attribute values of the each acceleration data segment and transmitting the calculated values to the output module.

As a further technical proposal of the invention, the fetal heart rate data preprocessing module also comprises:

an incorrect data processing unit used for processing incorrect data of the fetal heart rate data sequence, H(n), to obtain the effective fetal heart rate data sequence, V(n); and an interpolation processing unit used for fitting an invalid data part in the effective fetal heart rate data sequence, V(n) with a linear interpolation method to obtain the fetal heart rate data sequence, C(n).

As a further technical proposal of the invention, the fetal heart rate data acceleration recognition module also comprises:

a criteria comparison unit used for determining whether there is a sequence segment meeting a pre-configured acceleration determination criteria in the fetal heart rate data sequence, C(n);

an acceleration and variation unit used for inspecting and distinguishing the sequence segments of the variations between the accelerations and the baseline in the sequence C(n) meeting the criteria, according to the fetal heart rate data sequence C(n) meeting the determination criteria and the corresponding baseline sequence B(n) thereof; and an acceleration number analysis unit used for analyzing the continuous acceleration number of an acceleration sequence in the sequence C(n) meeting the criteria.

As a further technical proposal of the invention, the output module also comprises:

a display unit used for displaying a recognized acceleration data segment and an attribute value thereof;

a printing unit used for printing and outputting the recognized acceleration data segment and the attribute value thereof;

a storage unit used for storing the recognized acceleration data segment and the attribute value thereof; and a recognition unit used for recognizing the recognized acceleration data segment and the attribute value thereof.

A method for enhancing the accuracy of recognizing fetal heart rate data acceleration comprises:

Step 1, performing fetal heart rate data collection within a pre-configured duration to obtain a fetal heart rate data sequence, H(n);

Step 2, performing the baseline recognition on the fetal heart rate data sequence H(n) to obtain a fetal heart rate baseline data sequence, B(n);

Step 3, performing preprocessing on the fetal heart rate data sequence, H(n) to obtain a preprocessed fetal heart rate data sequence, C(n);

Step 4, performing acceleration recognition on the preprocessed fetal heart rate sequence, C(n) to obtain an acceleration data segment, according to pre-configured acceleration determination criteria and the fetal heart rate data baseline sequence, B(n); and Step 5, outputting each acceleration data segment and calculation results of the acceleration attribute value thereof.

As a further technical proposal in the invention, before Step 1, the method further comprises: collecting and processing a fetal heart signal, transforming it and obtaining the fetal heart rate data.

As a further technical proposal of the invention, Step 3 also comprises:

Step 31, processing incorrect data of the fetal heart rate data sequence H(n) to obtain a sequence, V(n); and Step 32, processing an interpolation of the sequence V(n) to obtain the preprocessed fetal heart rate data sequence, C(n).

As a further technical proposal of the invention, Step 4 also comprises:

Step 41, the sequences C(n) and B(n) are input into the pre-configured acceleration determination criteria, thus obtaining a set $\{\{C_i\}_{S_i}^{E_i}\}_1^N$ of each sequence segment meeting the acceleration criteria in the sequence, C(n) and the corresponding baseline sequence segment set $\{\{B_i\}_{S_i}^{E_i}\}_1^N$ thereof; if there is no sequence segment meeting the acceleration determination criteria, the user shall go back to Step 1 and collect the fetal heart rate data again;

Step 42, $\{C_i\}_{S_i}^{E_i}$ and $\{B_i\}_{S_i}^{E_i}$ are differenced to obtain sequence, segment $\{D_i\}_{S_i}^{E_i}$; the continuous sequence segment, which is not more than threshold $R_0$, is sought in the sequence segment $\{D_i\}_{S_i}^{E_i}$; if there is no sequence segment meeting the condition in $\{D_i\}_{S_i}^{E_i}$, the sequence segment $\{C_i\}_{S_i}^{E_i}$ is determined to be an acceleration sequence segment; if there is a sequence segment meeting the condition in $\{C_i\}_{S_i}^{E_i}$, the sequence segment at the corresponding place and in the $\{C_i\}_{S_i}^{E_i}$, meeting the condition, is determined as the baseline variation part which is recorded as $\{\{C'_j\}_{S'_j}^{E'_j}\}_1^M$; the baseline variation part divides the $\{C_i\}_{S_i}^{E_i}$ into a plurality of segments which are recorded as $\{\{\overline{C}_k\}_{\overline{S}_k}^{\overline{E}_k}\}_1^{N_2}$; it is determined whether $\{\overline{C}_k\}_{\overline{S}_k}^{\overline{E}_k}$ meets the deceleration criteria; if it meets the acceleration criteria, the $\{\overline{C'}_k\}_{\overline{S}'_k}^{E'_k}$ is recorded as the acceleration sequence segment, otherwise, it is the baseline variation sequence segment, wherein $R_0$ is a parameter set in advance; and Step 43, the continuous sequence segment, which deviates its corresponding baseline and of which the value exceeds threshold R1, is sought in the acceleration segment $\{\overline{C'}_k\}_{\overline{S}'_k}^{E'_k}$; if there is no sequence segment meeting such condition, the $\{\overline{C'}_k\}_{\overline{S}'_k}^{E'_k}$ is one acceleration; if there is a sequence segment meeting such condition, the $\{\{\overline{C''}_k\}_{\overline{S}''_k}^{E''_k}\}_1^{M_2}$ $\{\{\overline{C''}_k\}_{\overline{S}''_k}^{E''_k}\}_1^{M_2}$; and it is then analyzed whether each segment $\{\overline{C''}_k\}_{\overline{S}''_k}^{E''_k}$ separately meets the acceleration criteria; if the segment $\{\overline{C''}_k\}_{\overline{S}''_k}^{E''_k}$ may meet the acceleration criteria, the $\{\overline{C''}_k\}_{\overline{S}''_k}^{E''_k}$ separately becomes the acceleration; otherwise, the $\{\overline{C''}_k\}_{\overline{S}''_k}^{E''_k}$ is incorporated into the segment $\{\overline{C''}_k\}_{\overline{S}''_k}^{E''_k}$; its adjacent segments are facilitated to be continuous and analyzed together as to whether they meet the acceleration criteria; if the acceleration criteria is met, the continuous data segment becomes one acceleration, and the subsequent segment data is analyzed according to the acceleration criteria continuously again; otherwise, the baseline incorporates the segment until all of the segments are incorporated, wherein R1 is a pre-configured parameter.

As the further technical proposal of the invention, after Step 4, the method also comprises: determining the signal loss situation of each acceleration data segment and checking whether each acceleration sequence segment is in real acceleration, according to the acceleration data segment.

As the further technical proposal of the invention, after Step 4, the method also comprises: determining the signal loss situation of each acceleration data segment according to the acceleration data segment; and checking whether each acceleration sequence segment is in real acceleration; furthermore, the method comprises:

a. comparing the sequences V(n) and C(n) and marking an interpolation point to obtain a marked sequence, M(n);

b. as to each acceleration data segment, adjusting starting and destination points according to the sequence M(n) and facilitating the starting and destination points not to be the interpolation point and to be closest to the interpolation point;

c. calculating the adjusted signal loss degree S in the acceleration data segment and if the S exceeds threshold $\overline{S}$, the qualification of the acceleration is cancelled; otherwise, the interpolation area in acceleration is searched, and the duration T of the interpolation area and the average amplitude A of the interpolation value are calculated; if T is larger than threshold $\overline{T}$ or by L times larger than A, the interpolation area is regarded as an unacceptable area; otherwise it is an acceptable area, wherein $\overline{S}$, $\overline{T}$ and L are the parameters set in advance; and d. the acceleration data segment is divided into a plurality of areas by the unacceptable area and it is determined whether each area meets the pre-configured acceleration determination criteria; if it meets the criteria, it is determined to be in real acceleration; otherwise its acceleration qualification is cancelled.

As a further technical proposal of the invention, before Step 5, the method further comprises: calculating the acceleration attribute value of each acceleration data segment.

As a further technical proposal of the invention, before Step 5, calculating the acceleration attribute value of each acceleration data segment further comprises:

Step 51: calculating the maximum amplitude value deviating from the baseline in the acceleration data segment, according to the starting point, destination point and duration of each acceleration data segment; and Step 52, it is determined whether the uterine contraction data are collected at the same time. If the uterine contraction data are not collected, the type of the acceleration is not determined; if the uterine contraction data are collected, it is determined whether the starting point of the acceleration is bigger than that of the uterine contraction and whether the destination point of the acceleration is smaller than that of the uterine contraction at the same time; if the above two conditions are met, the acceleration is determined to be in periodic acceleration; otherwise, it is determined to be un-periodic acceleration.

As a further technical proposal of the invention, Step 6 further comprises: displaying and/or printing and/or storing and/or recognizing the acceleration data segment and the calculation results of the attribute values.

As a further technical proposal of the invention, the pre-configured acceleration determination criteria in Step 4 also comprises:

firstly, the fetal heart rate data segment to be analyzed shall all be above the fetal heart rate baseline;

secondly, the time, during which the amplitude deviating from the baseline exceeds A0, shall be equal to or bigger than T0;

thirdly, the maximum amplitude deviating from the baseline shall be equal to or bigger than A1; and fourthly, the energy of the fetal heart rate data segment to be analyzed shall be equal to or bigger than P0; wherein the energy is in direct proportion to the square of the amplitude and time and may be obtained through a numerical integration method.

If all of the above conditions are met, the fetal heart rate segment to be analyzed is an acceleration data segment, wherein A0, T0, A1 and P0 are the parameters set in advance.

With increased acceleration determining conditions and the adoption of a continuous peak inspection algorithm, the invention may effectively distinguish the variations between accelerations and the baseline, accurately recognize each acceleration in continuous accelerations, and avoid the situation where a detected number of fetal heart rate data acceleration is lower than the actual number or being mistaken due to current method, thereby enhancing accuracy in recognizing fetal heart rate curve acceleration. The method is suitable not only for cases where acceleration and a variation part of the baseline are independent but also cases where there are continuous accelerations and the variation part of the baseline is mixed in the acceleration.

BRIEF DESCRIPTION OF THE DRAWINGS

For easy description, the invention is described with the following preferred embodiments and drawings.

DETAILED DESCRIPTION OF THE EMBODIMENTS

In order that the objective, technical proposal and advantages of the invention are better described, the invention is further described in detail with the combination of drawings and embodiments in the following. It shall be understood that the embodiments described herein are merely used for explaining the invention and not used for limiting the invention.

Figure 1:
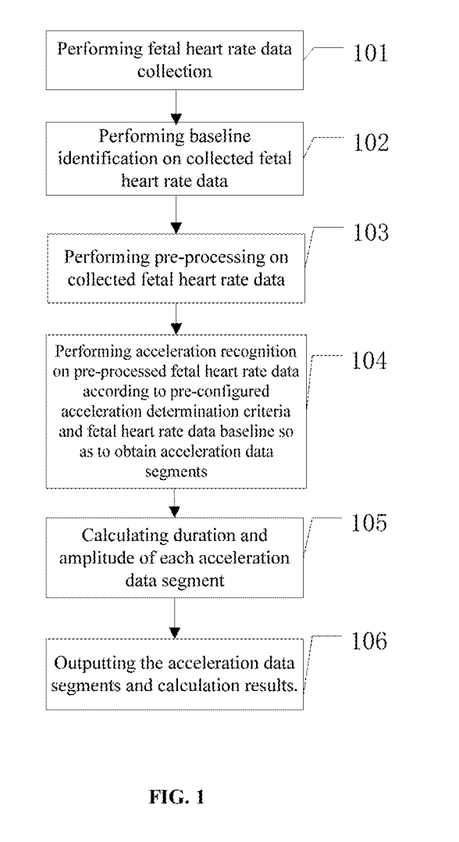
FIG. 1 is an embodiment flow chart of a method for enhancing the accuracy of recognizing a fetal heart rate data acceleration according to the invention.

The technical proposal for automatically recognizing fetal heart rate acceleration is realized mainly through an upper computer and a lower computer, wherein the lower computer collects a fetal heart rate signal mainly through an ultrasound probe and then calculates the fetal heart rate through a hardware filtered process and autocorrelation algorithm. The upper computer is mainly used for receiving the data from the lower computer and then displaying and storing the fetal heart rate data, depicting the fetal heart rate curve, as well as analyzing, displaying and printing the fetal heart rate data (comprising the recognition of fetal heart rate acceleration, etc.), wherein the main processing method is shown in FIG. 1:

101. Performing the Fetal Heart Rate Data Collection

The upper computer collects n-minute fetal heart rate data and obtains the fetal heart rate sequence, H(n), wherein in the example, at least ten minutes of data shall be collected. According to "Fetal Electronic Monitor", generally, at least ten minutes of data are needed to determine the fetal heart rate baseline.

102. Recognizing the Baseline of the Collected Fetal Heart Rate Data

Figure 5:
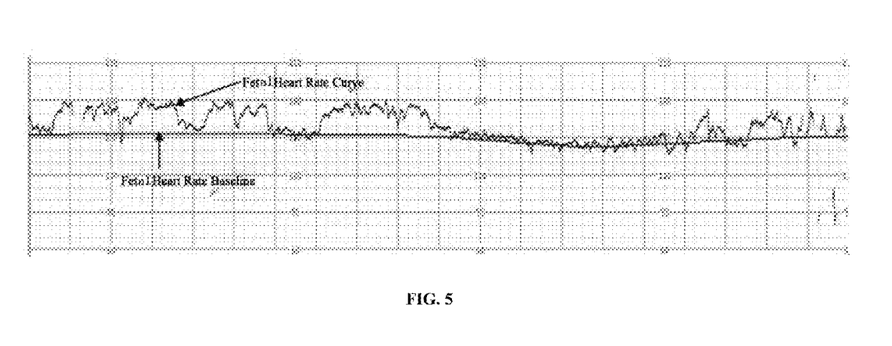
FIG. 5 is a schematic diagram of collected fetal heart rate data and a recognized fetal heart rate baseline.

According to the sequence, H(n), the fetal heart rate baseline data sequence, B(n) is recognized with the adoption of a low-pass filtered method. Comparing to the fetal heart rate data, the baseline belongs to the low frequency signal. A low-pass filter is characterized in that low-frequency signals may be passed through the filter while high-frequency signals may not be passed through the filter, thus extracting the low frequency signals of the fetal heart rate baseline. In addition, in this step, the data in the sequence, H(n) may also first be processed. After the data are processed with an incorrect data processing method, an average filtering method and a linear interpolation method, the fetal heart rate baseline is indentified according to the data. FIG. 5 shows collected fetal heart rate data and a recognized fetal heart rate baseline.

103. Performing Pre-Processing on the Collected Fetal Heart Rate Data

The sequence H(n) is processed with the incorrect data processing method and the linear interpolation method in sequence and then the fetal heart rate data sequence corresponding to different preprocessing processes are obtained.

104. The Accelerations of the Preprocessed Fetal Heart Rate Data are Recognized According to the Acceleration Determination Criteria and the Fetal Heart Rate Baseline to Obtain an Acceleration Data Segment.

The sequence segment meeting the conditions is determined according to preprocessed determination criteria. According to the sequence segment and the corresponding baseline sequence segment thereof, the sequence segments of the variations between accelerations and baseline in the sequence segment are inspected and distinguished, and the number of continuous accelerations of the acceleration sequence segment is analyzed.

105. Calculating the Acceleration Attribute Values of Each Acceleration Data Segment:

According to the starting point, destination point and duration of each acceleration, the maximum amplitude value deviating from the baseline in the acceleration is calculated.

106. Outputting the Acceleration Data Segment and the Calculated Results:

The example preferably displays and/or prints and/or stores the recognized acceleration data segment and the calculated results.

Figure 2:
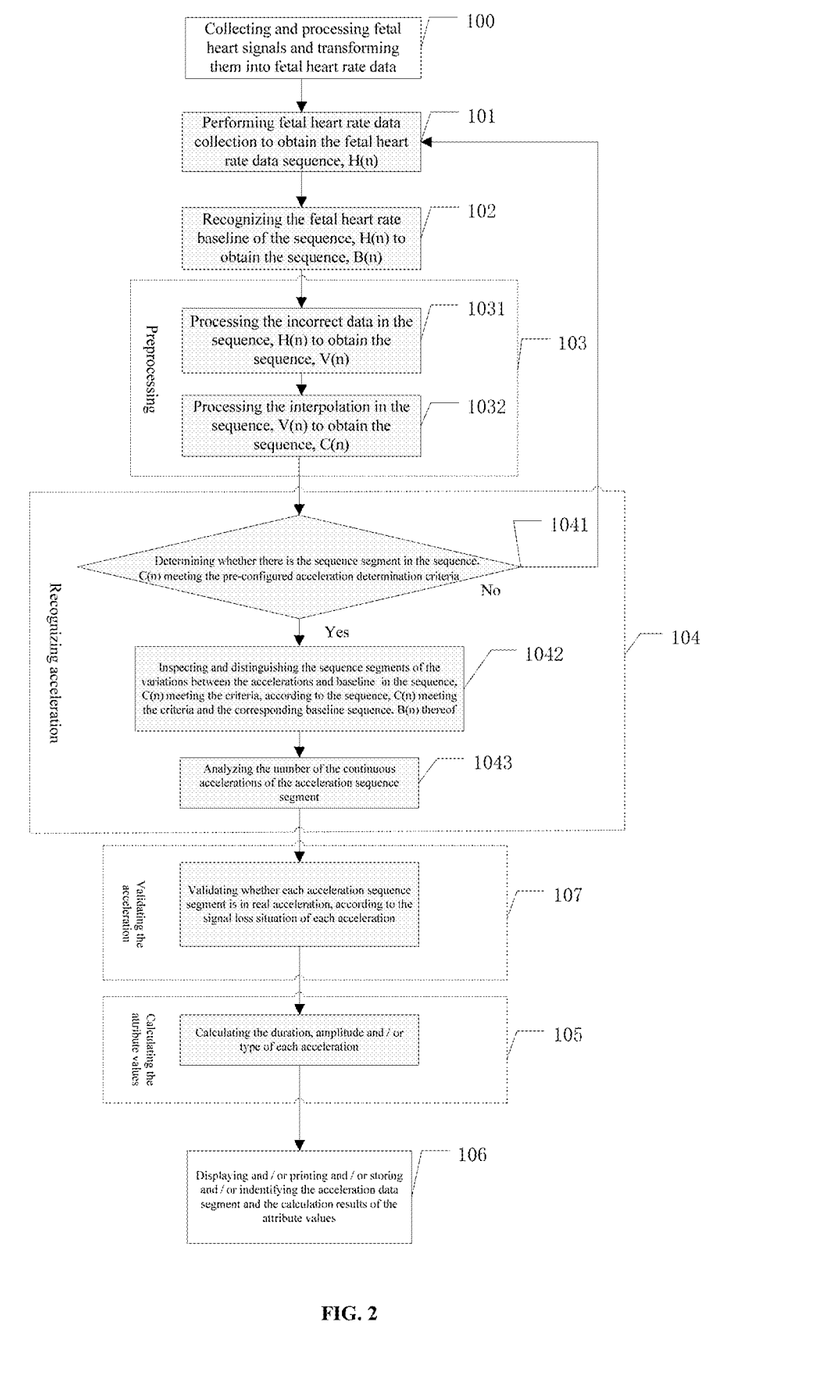
FIG. 2 is an another embodiment flow chart of a method for enhancing the accuracy of recognizing a fetal heart rate data acceleration according to the invention.

In order to better understand the invention, as another example of the invention, FIG. 2 shows the flow chart of a method for enhancing the accuracy of recognizing fetal heart rate data acceleration in the following:

100. Collecting and Processing a Fetal Heart Signal and Transforming it into the Fetal Heart Rate Data:

After the fetal heart signal is received by an ultrasound probe in the lower computer, it is filtered by hardware and the fetal heart rate is calculated according to an autocorrelation algorithm and uploaded to the upper computer. The processing of the upper computer comprises: displaying, storing and depicting the fetal heart rate data into a fetal heart rate curve and processing the related data, etc., wherein the hardware filtering is used for removing the frequency interference of the collected signals, and the autocorrelation algorithm is characterized in that it may strengthen a periodic signal and weakens stochastic noise, which are the general techniques for calculating fetal heart rate data.

101. Performing Fetal Heart Rate Data Collection to Obtain the Fetal Heart Rate Data Sequence, H(n):

The upper computer collects n-minute fetal heart rate data and obtains the fetal heart rate sequence, H(n), wherein in the example, at least ten minutes of data shall be collected. According to "Fetal Electronic Monitor", generally, at least ten minutes of data are needed to determine the fetal heart rate baseline.

102. Recognizing the Fetal Heart Rate Baseline in the Sequence, H(n), to Obtain the Sequence, B(n);

According to the sequence, H(n), the fetal heart rate baseline B(n) is recognized with the adoption of a low-pass filtering method. Comparing to the fetal heart rate data, the baseline belongs to the low frequency signal. A low-pass filter is characterized in that low-frequency signals may be passed through the filter while high-frequency signals may not be passed through the filter, thus extracting the low frequency signals of the fetal heart rate baseline. In addition, in this step, the data in the sequence H(n) may also first be processed. After the data are processed with an incorrect data processing method, an average filtering method and a linear interpolation method, the fetal heart rate baseline is identified according to the data. FIG. 5 shows collected fetal heart rate data and a recognized fetal heart rate baseline. In addition, there are many methods for recognizing the fetal heart rate data baseline, for example, an averaging method generally adopted in the industry, etc.

1031. Processing the Incorrect Data in the Sequence H(n) and Obtaining the Sequence V(n):

The incorrect data in the sequence H(n) are processed to obtain the effective fetal heart rate data sequence, V(n). This step may effectively filter out invalid and incorrect data in the fetal heart sequence generated because of poor quality of the fetal heart signals, and the remainder are valid data.

Figure 6:
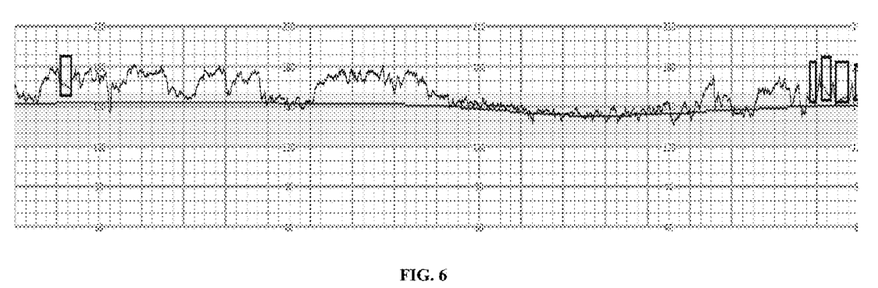
FIG. 6 is an effect picture of a preprocessed fetal heart rate data sequence.

1032. Processing the Sequence V(n) with Interpolation to Obtain the Sequence C(n):

The invalid data in the sequence V(n) are fitted with a linear interpolation method to obtain the sequence C(n). The linear interpolation method is a simple interpolation method in which other points in a straight line are obtained with a principle of forming a straight line by connecting two points. FIG. 6 is an effect diagram of a preprocessed fetal heart rate data sequence. The fetal heart rate curve part in a square frame in the Figure is just the curve section obtained after the incorrect data are processed with the interpolation.

In Steps 1031 and 1032, the collected fetal heart rate data are preprocessed. In addition, the fetal heart rate data preprocessing step is not limited to the above steps. It can also adopt the following methods known in the industry: the fetal heart rate value with bpm (beats per min) as the unit dividing with incorrect data and/or moving average and/or interpolation fitting, etc.

1041. It is Determined Whether there is a Sequence Segment in the Sequence C(n) Meeting the Pre-Configured Acceleration Determination Criteria:

The deceleration determination criteria which are preferably pre-configured in the example are as follows:

As to one section of the fetal heart rate curve, it may be determined to be in acceleration only when it meets all of the following conditions:

firstly: The fetal heart rate curves of the segment shall all be above the fetal heart rate baseline;

secondly, the time during which the amplitude deviates from the baseline by more than A0, shall be equal to or bigger than T0;

thirdly, the maximum amplitude deviating from the baseline shall be equal to or bigger than A1;

fourthly, the energy of the fetal heart rate curve shall be bigger than P0, wherein the energy is in direct proportion to the square of the amplitude and time and may be obtained through a numerical integration method.

The determination condition enhances the determination criteria, thus facilitating the determination to be more accurate. The parameters A0, T0, A1 and P0 are pre-configured experiential parameters and set differently with different input of the gestational week parameters.

The sequences C(n) and B(n) are input into the acceleration determination criteria, thus obtaining the set $\{\{C_i\}_{S_i}^{E_i}\}_1^N$ of each sequence segment meeting the acceleration criteria in the sequence C(n) and the corresponding baseline sequence segment set $\{\{B_i\}_{S_i}^{E_i}\}_1^N$ thereof. If there is not the sequence segment meeting the acceleration criteria, it means that there is no acceleration in the fetal heart rate curve. At this time, the recognition of the fetal heart rate acceleration may end and the fetal heart rate data is collected once again.

1042. According to the sequence C(n) meeting the criteria and the corresponding baseline sequence, B(n) thereof, the sequence segments of the variations between the accelerations and baseline in sequence C(n) meeting the criteria are inspected and distinguished.

As to each sequence segment $\{C_i\}_{S_i}^{E_i}$, $\{C_i\}_{S_i}^{E_i}$ and $\{B_i\}_{S_i}^{E_i}$ are differenced to obtain the sequence segment $\{D_i\}_{S_i}^{E_i}$. The continuous sequence segment, which is not more than threshold $R_0$, is sought in the sequence segment $\{D_i\}_{S_i}^{E_i}$. If there is no sequence segment in the sequence $\{D_i\}_{S_i}^{E_i}$ meeting the condition, the sequence segment $\{C_i\}_{S_i}^{E_i}$ consists of one acceleration group or continuous acceleration group. The number of accelerations is analyzed with a continuous peak inspection algorithm method in the next step. If there is a sequence segment meeting the condition in $\{C_i\}_{S_i}^{E_i}$, the sequence segment at the corresponding place and in the $\{C_i\}_{S_i}^{E_i}$ is determined as the baseline variation part which is recorded as $\{\{C'_j\}_{S'_j}^{E'_j}\}_1^M$, wherein $\{C'_j\}_{S'_j}^{E'_j} \subseteq \{C_i\}_{S_i}^{E_i}$. At this time, the baseline variation part divides the $\{C_i\}_{S_i}^{E_i}$ into a plurality of segments which are recorded as $\{\{\overline{C'}_k\}_{\overline{S}_k}^{\overline{E'}_k}\}_1^{N_2}$, wherein $\{\overline{C'}_k\}_{\overline{S}_k}^{\overline{E'}_k} \subseteq \{C_i\}_{S_i}^{E_i}$. It is determined whether $\{\overline{C'}_k\}_{\overline{S}_k}^{\overline{E'}_k}$ meets the acceleration criteria. If it meets the acceleration criteria, $\{\overline{C'}_k\}_{\overline{S}_k}^{\overline{E'}_k}$ is one acceleration group or continuous acceleration group, and the number of accelerations is analyzed with a continuous peak inspection algorithm in the next step. If it does not meet the deceleration criteria, $\{\overline{C'}_k\}_{\overline{S}_k}^{\overline{E'}_k}$ with this step, the variations between the accelerations and the baseline may be distinguished.

Figure 7:
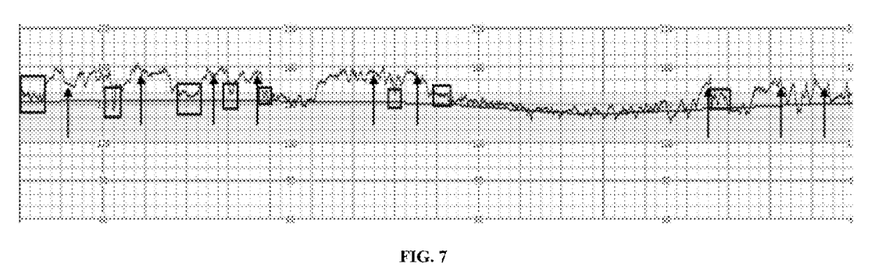
FIG. 7 is an effect picture of an acceleration recognition of a fetal heart rate data sequence.

1043. Analyzing the Number of Continuous Accelerations of the Acceleration Sequence Segment:

As to the fetal heart rate sequence segment (here, it may be $\{C_i\}_{S_i}^{E_i}$ or $\{\overline{C'}_k\}_{S'_k}^{E'_k}$) to be analyzed, there is $\{\overline{C'}_k\}_{\overline{S}_k}^{E'_k} \subseteq \{C_i\}_{S_i}^{E_i}$. The process analyzed with the continuous peak inspection algorithm is as follows: The continuous sequence segment, of which the deviation value of the corresponding baseline is not more than the threshold R1, is sought in the segment. If there is no sequence segment (all deviation values exceed the threshold R1) meeting such condition, the $\{\overline{C'}_k\}_{\overline{S}_k}^{E'_k}$ is one acceleration. If there is a sequence segment meeting such condition, the $\{\{\overline{C''}_k\}_{\overline{S}_k}^{E''_k}\}_1^{M_2}$ $\{\overline{C''}_k\}_{\overline{S}_k}^{E''_k} \subseteq \{\overline{C'}_k\}_{\overline{S}_k}^{E'_k}$, wherein $\{\overline{C''}_k\}_{\overline{S}_k}^{E''_k} \subseteq \{\overline{C'}_k\}_{\overline{S}_k}^{E'_k}$ and it is then analyzed whether each the segment $\{\overline{C''}_k\}_{\overline{S}_k}^{E''_k}$ separately meets the acceleration criteria; if the segment $\{\overline{C''}_k\}_{\overline{S}_k}^{E''_k}$ may meet the acceleration criteria, the $\{\overline{C''}_k\}_{\overline{S}_k}^{E''_k}$ separately becomes the acceleration; otherwise, the $\{\overline{C''}_k\}_{\overline{S}_k}^{E''_k}$ is incorporated into the segment $\{\overline{C''}_k\}_{\overline{S}_k}^{E''_k}$; its adjacent segments are facilitated to be continuous and analyzed together as to whether they meet the acceleration criteria; if the acceleration criteria is met, the continuous data segment becomes one acceleration, and the subsequent segment data is analyzed according to the acceleration criteria continuously again; otherwise, the baseline incorporates the segment until all of the segments are incorporated. With this step, a continuous acceleration is recognized. FIG. 7 is an effective diagram of acceleration recognition. The fetal heart rate curve part in the square frame in the figure is the variation part of the baseline. The curve segment part designated with the arrow is the recognized fetal heart rate acceleration curve segment.

The abovementioned Steps 1041, 1042 and 1043 are used for recognizing the acceleration of the processed and collected fetal heart rate data. So far, this step has completed the recognition on the acceleration data segment of the invention. Steps 105 and 106 may be directly entered to calculate the attribute values and output the results, or Step 106 may be directly entered into to output the calculated results. In order to facilitate the results to be more accurate, the example also may preferably adopt the following acceleration validation steps prior to the steps of calculation and result output.

Figure 8:
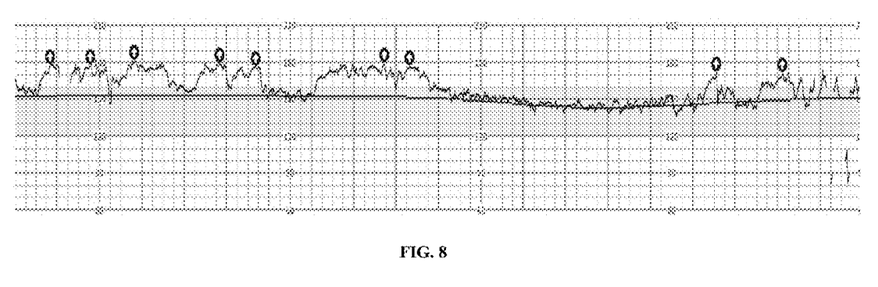
FIG. 8 is an effect picture of an acceleration validation of a fetal heart rate data sequence.

107. It is Validated Whether Each Acceleration Sequence Segment is in Real Acceleration According to the Signal Loss Situation of Each Acceleration:

If the acceleration of the above steps is obtained according to the interpolated sequence, it means that the acceleration is obtained without consideration of the signal loss. In the step, the acceleration shall be validated and the signal loss in each pre-acceleration shall be analyzed, thus determining whether each pre-acceleration is retained and split, and finally obtaining the real acceleration. The step also comprises the following processes:

The first step: comparing the sequences V(n) and C(n) and marking an interpolation place to obtain a marked sequence, M(n);

The second step: as to each acceleration, adjusting the places of starting and destination points of the acceleration according to the sequence M(n) and facilitating the starting and destination points not to be the interpolation point and to be closest to the interpolation point;

The third step: the adjusted signal loss degree S calculated is the number (being equal to the number of the interpolation points) of the invalidated values in the fetal heart rate acceleration curve data and the proportion of the invalidated values against the whole part. If S exceeds the threshold S, the qualification of the acceleration shall be cancelled. Otherwise, the interpolation area in acceleration is searched, and the duration T of the interpolation area and the average amplitude A of the interpolation value are calculated; if T is larger than threshold T or by L times larger than A, the interpolation area is regarded as an unacceptable area; otherwise it is an acceptable area;

The fourth step: the acceleration data segment is divided into a plurality of areas by the unacceptable area. It is determined whether each area meets the acceleration criteria. If it meets the criteria, it is determined to be in real acceleration; otherwise its acceleration qualification is cancelled. FIG. 8 is an effective diagram of acceleration validation. The arrow icon in the figure indicates acceleration.

105. Calculating the Duration, Amplitude and/or Type of Each Acceleration:

According to the starting point, destination point and duration of each acceleration, the maximum amplitude value deviating from the baseline in the acceleration is calculated.

Figure 9:
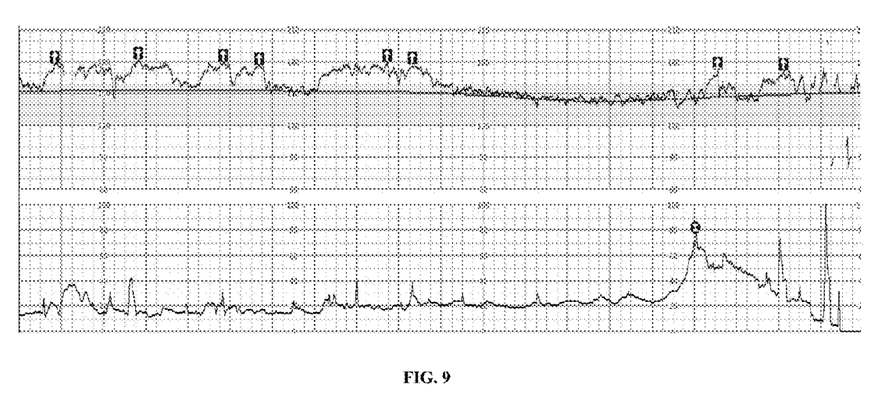
FIG. 9 is an effect picture of a recognition of the acceleration type of a fetal heart rate data sequence when there are uterine contraction data.

In addition, if the type of acceleration may be determined while the uterine contraction data are collected, then if the uterine contraction data are not collected, the type of the acceleration is not determined and the final acceleration displaying effective diagram is in line with FIG. 8. If the uterine contraction data are collected, it is determined whether the starting point of the acceleration is bigger than that of the uterine contraction and whether the destination point of the acceleration is smaller than that of the uterine contraction at the same time; if the above two conditions are met, the acceleration is determined to be in periodic acceleration; otherwise, it is determined to be un-periodic acceleration. FIG. 9 is an effective diagram of the acceleration display when there are uterine contraction data. In the drawings,  represents periodic acceleration;  represents non-periodic acceleration, and  represents uterine contraction.

106: Displaying and/or Printing and/or Storing and/or Recognizing the Acceleration Data Segment and the Calculation Results of Attribute Values:

The indentified acceleration data segments are respectively input into a displaying module, a printing module and a storage module. Each acceleration data segment and the attribute values thereof are also recognized and displayed in the fetal monitoring drawing. Its attribute values may be stored and printed.

Figure 3:
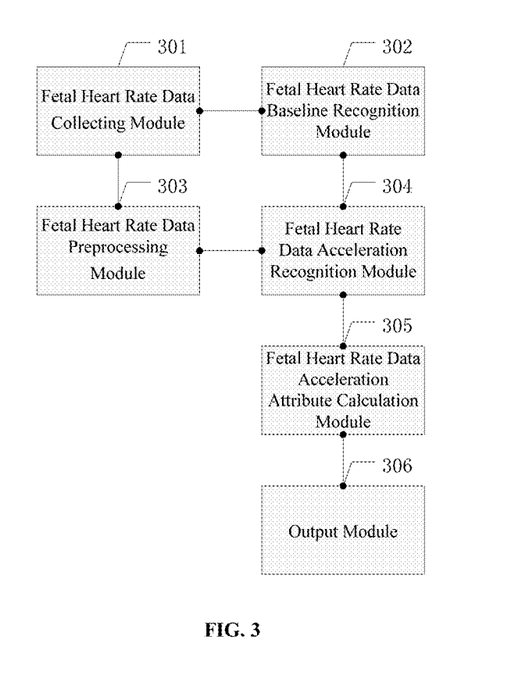
FIG. 3 is an example site structure of a device for enhancing the accuracy of recognizing a fetal heart rate data acceleration according to the invention.

In order to better explain the invention, an example site structure of a device for enhancing the accuracy of recognizing a fetal heart rate data acceleration is provided, which is shown in FIG. 3:

A Fetal Heart Rate Data Collecting Module 301:
The module 301 is used for performing the fetal heart rate data collection with pre-configured duration to obtain the fetal heart rate data sequence, H(n);

A Fetal Heart Rate Data Baseline Recognition Module 302:
The module 302 is connected with the fetal heart rate data collecting module 301 and used for receiving the fetal heart rate data sequence H(n) transmitted by the fetal heart rate data collecting module 301 and recognizing the fetal heart rate baseline sequence, B(n);

A Fetal Heart Rate Data Preprocessing Module 303:
The module 303 is connected with the fetal heart rate data collecting module 301 and used for receiving the fetal heart rate data sequence H(n) transmitted by the fetal heart rate data collecting module 301, and performing preprocessing on the sequence H(n) to obtain the fetal heart rate data sequence, V(n);

A Fetal Heart Rate Data Acceleration Recognition Module 304:
The fetal heart rate data baseline recognition module 302 is connected with the fetal heart rate data preprocessing module 303 and used for receiving the fetal heart rate data baseline sequence B(n) transmitted by the fetal heart rate data baseline recognition module 302 and the preprocessed sequence V(n) transmitted by the fetal heart rate data preprocessing module 303. The acceleration recognition on the preprocessed fetal heart rate data sequence V(n) is performed to obtain an acceleration data segment, according to the pre-configured acceleration determination criteria and the fetal heart rate data baseline sequence, B(n), and A Fetal Heart Rate Data Acceleration Attribute Calculation Module 305:
The module 305 is connected with the fetal heart rate data acceleration recognition module 304 and used for receiving the acceleration data segment transmitted by the fetal heart rate data acceleration recognition module 304 and calculating the duration, amplitude and other acceleration attributes of each acceleration data segment.

An Output Module 306:
The output module 306 is connected with the fetal heart rate data acceleration attribute calculation module 305 and used for receiving the acceleration data segment and the acceleration attribute calculation results thereof transmitted by the fetal heart rate data acceleration attribute calculation module 305, and outputting them.

Figure 4:
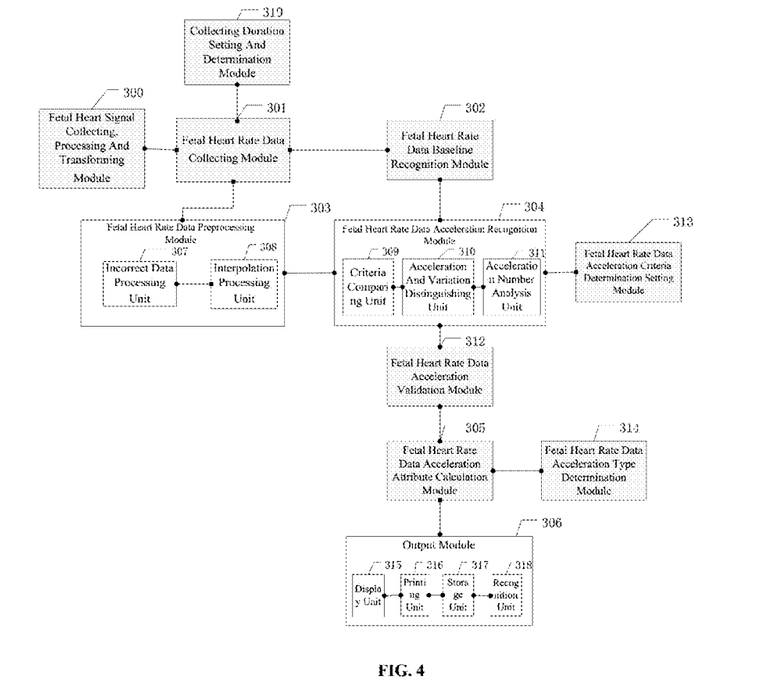
FIG. 4 is an another example site structure of a device for enhancing the accuracy of recognizing a fetal heart rate data acceleration according to the invention.

In order to better explain the invention, another example structure of a device for enhancing the accuracy of recognizing a fetal heart rate data acceleration is provided, which is shown in FIG. 4:

A device for enhancing accuracy of recognizing fetal heart rate acceleration also comprises:

A Fetal Heart Signal Collecting, Processing and Transforming Module 300:
The module 300 is connected with the fetal heart rate data collecting module 301, is an ultrasound probe device realizing the collection, process and transformation of the signals, as well as for collecting the fetal heart signals, transforming them into the fetal heart rate data and transmitting the fetal heart rate data to the fetal heart rate data collecting module 301.

A Fetal Heart Rate Data Acceleration Validation Module 312:
The module 312 is connected with the fetal heart rate data acceleration recognition module 304 and the fetal heart rate data acceleration attribute calculation module 305 and is used for receiving the acceleration data segment transmitted by the fetal heart rate data acceleration recognition module 304, validating whether each acceleration sequence segment is real acceleration according to the signal loss situation of each acceleration, and transmitting the validated results to the fetal heart rate data acceleration attribute calculation module 305.

A Fetal Heart Rate Data Acceleration Determination Criteria Setting Module 313:

The module 313 is connected with the fetal heart rate data acceleration recognition module 304 and used for setting the fetal heart rate data acceleration determination criteria in advance and transmitting the criteria to the fetal heart rate data acceleration module 304.

A fetal heart rate data acceleration type determination module 314:

The module 314 is connected with the fetal heart rate data acceleration attribute calculation module 305 and used for determining the acceleration type under the conditions of collecting the uterine contraction data, and transmitting the determined results to the fetal heart rate data acceleration attribute calculation module 305.

A Collecting Duration Setting and Determination Module 319:

The module 319 is connected with the fetal heart rate data collecting module 301 and used for setting the collecting duration of the fetal heart rate data, and determining whether the collected data time exceeds the set duration. If it exceeds the set duration, a timeout signal is transmitted to the fetal heart rate data collecting module 301.

In addition, the fetal heart rate data preprocessing module 303 further comprises:

an incorrect data processing unit 307 used for processing the incorrect data of the fetal heart rate data sequence, H(n), to obtain the effective fetal heart rate data sequence, V(n);

an interpolation processing unit 308 used for fitting an invalid data part in the effective fetal heart rate data sequence V(n) with a linear interpolation method to obtain the fetal heart rate data sequence, C(n).

the fetal heart rate data acceleration recognition module 304 further comprises:

a criteria comparison unit 309 used for determining whether there is a sequence segment meeting a pre-configured acceleration determination criteria in the feta heart rate data sequence C(n);

an acceleration and variation unit 310 used for inspecting and distinguishing the sequence segment of the variations between the accelerations and baseline in the sequence C(n) meeting the criteria, according to the fetal heart data sequence C(n) meeting the determination criteria and the corresponding baseline sequence B(n) thereof; and an acceleration number analysis unit 311 used for analyzing the number of continuous accelerations of an acceleration sequence segment in the sequence C(n) meeting the criteria.

the output module 306 further comprises:

a display unit 315 used for displaying a recognized acceleration data segment and an attribute value thereof;

a printing unit 316 used for printing and outputting the recognized acceleration data segment and the attribute value thereof;

a storage unit 317 used for storing the recognized acceleration data segment and the attribute value thereof; and a recognition unit 318 used for recognizing the recognized acceleration data segment and the attribute value thereof.

The abovementioned examples are only the preferred examples of the invention and do not limit the invention. Any modification, equal replacement and enhancement within the spirit and principle of the invention shall be included in the scope of protection of the invention.

The invention claimed is:

1. A device for enhancing the accuracy of recognizing fetal heart rate data acceleration, wherein the device comprises a fetal heart rate data collecting module, a fetal heart rate data baseline recognition module, a fetal heart rate data preprocessing module, a fetal heart rate data acceleration recognition module and an output module;

wherein the fetal heart rate data collecting module is configured for performing the fetal heart rate data collection in a pre-configured period to obtain a fetal heart rate data sequence, H(n);

wherein the fetal heart rate data baseline recognition module is connected with the fetal heart rate data collecting module and configured for receiving the fetal heart rate data sequence, H(n) transmitted by the fetal heart rate data collecting module and recognizing a fetal heart rate baseline sequence, B(n);

wherein the fetal heart rate data preprocessing module is connected with the fetal heart rate data collecting module and configured for receiving the fetal heart rate data sequence, H(n), transmitted by the fetal heart rate data collecting module and performing preprocessing on the sequence H(n) to obtain a fetal heart rate data sequence, V(n);

wherein the fetal heart rate data acceleration recognition module is connected with the fetal heart rate data baseline recognition module and the fetal heart rate data preprocessing module and configured for receiving the fetal heart rate baseline sequence, B(n), transmitted by the fetal heart rate data baseline recognition module and the preprocessed sequence, V(n), transmitted by the fetal heart rate data preprocessing module; the acceleration recognition on the preprocessed fetal heart rate data sequence V(n) is performed to obtain an acceleration data segment, according to a pre-configured acceleration determination criteria and the fetal heart rate data baseline sequence, B(n);

wherein the fetal heart rate data acceleration recognition module comprises a criteria comparison unit configured for determining whether there is a sequence segment meeting a pre-configured acceleration determination criteria in the fetal heart rate data sequence, C(n), an acceleration and variation unit configured for inspecting and distinguishing the sequence segments of the variation between acceleration and baseline in the sequence C(n) meeting the criteria, according to the fetal heart rate data sequence C(n) meeting the determination criteria and the corresponding baseline sequence B(n) thereof, and an acceleration number analysis unit configured for analyzing the continuous acceleration number of an acceleration sequence in the sequence C(n) meeting pre-configured acceleration determination criteria; and wherein the output module is connected with the fetal heart rate data acceleration recognition module and configured for receiving the acceleration data segment transmitted by the fetal heart rate data acceleration recognition module and outputting the acceleration data segment.

2. The device for enhancing the accuracy of recognizing fetal heart rate data acceleration according to claim 1, wherein the device for enhancing the accuracy of recognizing fetal heart rate data acceleration also comprises a fetal heart rate signal collecting and processing transforming module, a fetal heart rate data acceleration validation module, a fetal heart rate data acceleration determination criteria setting module, a fetal heart rate data acceleration type determination module, a collecting duration setting and determination module and a fetal heart rate data acceleration attribute calculation module, wherein the fetal heart rate signal collecting and processing transforming module is connected with the fetal heart rate data collecting module and configured for collecting a fetal heart signal, transforming the signal into the fetal heart rate data and transmitting the fetal heart rate data to the fetal heart rate data collecting module;

the fetal heart rate data acceleration validation module is connected with the fetal heart rate data acceleration recognition module and the fetal heart rate data acceleration attribute calculation module and configured for receiving the acceleration data segment transmitted by the fetal heart rate data acceleration recognition module; according to the signal loss condition of each acceleration, the fetal heart rate data acceleration validation module validates whether each acceleration sequence segment is in real acceleration, and transmits the validation result to the fetal heart rate data acceleration attribute calculation module;

the fetal heart rate data acceleration determination criteria setting module is connected with the fetal heart rate acceleration recognition module and configured for setting the fetal heart rate data acceleration determination criteria in advance and transmitting the determination criteria to the fetal heart rate data acceleration recognition module;

the fetal heart rate data acceleration type determination module is connected with the fetal heart rate data acceleration attribute calculation module and configured for determining the acceleration type under the conditions of simultaneously collecting uterine contraction data and transmitting the determination result to the fetal heart rate data acceleration calculation module;

the collecting duration setting and determination module is connected with the fetal heart rate data collecting module and configured for setting the collecting duration of the fetal heart rate data, and determining whether the collected data time exceeds the set duration and if it exceeds the set duration, a timeout signal is transmitted to the fetal heart rate data collecting module; and the fetal heart rate data acceleration attribute calculation module is connected with the fetal heart rate data acceleration recognition module and the output module and configured for receiving the acceleration data segment transmitted by the fetal heart rate data acceleration recognition module, calculating the duration, amplitude and other acceleration attribute values of each acceleration data segment and transmitting the calculated values to the output module.

3. The device for enhancing the accuracy of recognizing fetal heart rate data acceleration according to claim 1, wherein the fetal heart rate data preprocessing module further comprises:

an incorrect data processing unit configured for processing the incorrect data of the fetal heart rate data sequence, H(n), to obtain the effective fetal heart rate data sequence, V(n); and an interpolation processing unit configured for fitting an invalid data part in the effective fetal heart rate data sequence, V(n) with a linear interpolation method to obtain the fetal heart rate data sequence, C(n).

4. The device for enhancing the accuracy of recognizing fetal heart rate data acceleration according to claim 1, wherein the output module further comprises:

a display unit configured for displaying a recognized acceleration data segment and an attribute value thereof;

a printing unit configured for printing and outputting the recognized acceleration data segment and the attribute value thereof;

a storage unit configured for storing the recognized acceleration data segment and the attribute value thereof; and a recognition unit configured for recognizing the recognized acceleration data segment and the attribute value thereof.

5. A method for enhancing the accuracy of recognizing fetal heart rate data acceleration, wherein the method comprises:

performing fetal heart rate data collection within pre-configured duration to obtain a fetal heart rate data sequence, H(n);

performing baseline recognition on the fetal heart rate data sequence H(n) to obtain a fetal heart rate baseline data sequence, B(n);

performing preprocessing on the fetal heart rate data sequence H(n) to obtain a preprocessed fetal heart rate data sequence, C(n);

performing acceleration recognition on the preprocessed fetal heart rate sequence C(n) to obtain an acceleration data segment, according to pre-configured acceleration determination criteria and the fetal heart rate data baseline sequence, B(n), by inputting the sequences C(n) and B(n) into the pre-configured acceleration determination criteria, thus obtaining a set $\{\{C_i\}_{S_i}^{E_i}\}_1^N$ of each sequence segment meeting the acceleration criteria in the sequence C(n) and the corresponding baseline sequence segment set $\{\{B_i\}_{S_i}^{E_i}\}_1^N$ thereof if there is not sequence segment meeting the acceleration determination criteria, the user shall collect the fetal heart rate data again; $\{C_i\}_{S_i}^{E_i}$ and $\{B_i\}_{S_i}^{E_i}$ to obtain sequence segment $\{D_i\}_{S_i}^{E_i}$; the continuous sequence segment, which is not more than threshold $R_0$, is sought in the sequence segment $\{D_i\}_{S_i}^{E_i}$; if there is not sequence segment meeting the condition in $\{D_i\}_{S_i}^{E_i}$, the sequence segment $\{C_i\}_{S_i}^{E_i}$ is determined to be an acceleration sequence segment if there is a sequence segment meeting the condition in $\{C_i\}_{S_i}^{E_i}$, the sequence segment at the corresponding place and in the $\{C_i\}_{S_i}^{E_i}$, meeting the condition, is determined as the baseline variation part which is recorded as $\{\{C'_j\}_{S'_j}^{E'_j}\}_1^M$; the baseline variation part divides the $\{C_i\}_{S_i}^{E_i}$ into a plurality of segments which are recorded as $\{\{\overline{C}_k\}_{\overline{S}_k}^{\overline{E}_k}\}_1^{N_2}$; it is determined whether $\{\overline{C}_k\}_{\overline{S}_k}^{\overline{E}_k}$ meets the deceleration criteria; if it meets the acceleration criteria, the $\{\overline{C}_k\}_{\overline{S}_k}^{\overline{E}_k}$ is recorded as the acceleration sequence segment, otherwise, it is the sequence segment of the variation of the baseline, wherein $R_0$ is a parameter set in advance; the continuous sequence segment, which deviates its corresponding baseline and of which the value exceeds threshold R1, is sought in the acceleration segment $\{\overline{C}_k\}_{\overline{S}_k}^{\overline{E}_k}$; if there is not sequence segment meeting such condition, the $\{\overline{C}_k\}_{\overline{S}_k}^{\overline{E}_k}$ is one acceleration; if there is a sequence segment meeting such condition, recording as $\{\{\overline{C}''_k\}_{\overline{S}''_k}^{\overline{E}''_k}\}_1^{M_2}$; and it is then analyzed whether each segment $\{\overline{C}''_k\}_{\overline{S}''_k}^{\overline{E}''_k}$ separately meets the acceleration criteria; if the segment $\{\overline{C}''_k\}_{\overline{S}''_k}^{\overline{E}''_k}$ may meet the acceleration criteria, the $\{\overline{C''}_k\}_{\overline{S''}_k}^{E''_k}$ separately becomes the acceleration; otherwise, the $\{\overline{C''}_k\}_{\overline{S''}_k}^{E''_k}$ is incorporated into the segment $\{\overline{C''}_k\}_{\overline{S''}_k}^{E''_k}$; its adjacent segments are facilitated to be continuous and analyzed together as to whether they meet the acceleration criteria; if the acceleration criteria is met, the continuous data segment becomes one acceleration, and the subsequent segment data is analyzed according to the acceleration criteria continuously again; otherwise, the baseline incorporates the segment until all of the segments are incorporated, wherein R1 is a pre-configured parameter; and outputting each acceleration data segment and calculation results of the acceleration attribute value thereof.

6. The method for enhancing the accuracy of recognizing the fetal heart rate data acceleration according to claim 5, wherein before performing fetal heart rate data collection, the method further comprises: collecting and processing a fetal heart signal, transforming the fetal heart signal and obtaining the fetal heart rate data.

7. The method for enhancing the accuracy of recognizing fetal heart rate data acceleration according to claim 5, wherein performing processing further comprises:
    processing incorrect data of the fetal heart rate data sequence H(n) to obtain a sequence, V(n); and
    processing an interpolation of the sequence V(n) to obtain the preprocessed fetal heart rate data sequence, C(n).

8. The method for enhancing the accuracy of recognizing fetal heart rate data acceleration according to claim 5, wherein after performing acceleration recognition, the method also comprises: determining the signal loss situation of each acceleration data segment and checking whether each acceleration sequence segment is in real acceleration, according to the acceleration data segment.

9. The method for enhancing the accuracy of recognizing fetal heart rate data acceleration according to claim 8, wherein determining, the signal loss situation of each acceleration data segment, and checking whether each acceleration sequence segment is in real acceleration further comprises:
    a. comparing the sequences V(n) and C(n) and marking an interpolation point to obtain a marked sequence, M(n);
    b. as to each acceleration data segment, adjusting starting and destination points according to the sequence M(n) and facilitating the starting and destination points not to be the interpolation point and to be closest to the interpolation point; and
    c. calculating the adjusted signal loss degree S in the acceleration data segment and if the S exceeds threshold $\overline{S}$, the qualification of the acceleration is cancelled; otherwise, the interpolation area in acceleration is searched, and the duration T of the interpolation area and average amplitude A of the interpolation value are calculated; if T is larger than threshold $\overline{T}$ or by L times larger than A, the interpolation area is regarded as an unacceptable area; otherwise it is an acceptable area, wherein $\overline{S}$, $\overline{T}$ and L are the parameters set in advance; and
    d. the acceleration data segment is divided into a plurality of areas by the unacceptable area and it is determined whether each area meets the pre-configured acceleration determination criteria; if it meets the criteria, it is determined to be in real acceleration; otherwise its acceleration qualification is cancelled.

10. The method for enhancing the accuracy of recognizing fetal heart rate data acceleration according to claim 5, wherein before outputting the acceleration data segment and calculation results, the method further comprises: calculating the acceleration attribute value of each acceleration data segment.

11. The method for enhancing the accuracy of recognizing fetal heart rate data acceleration according to claim 10, wherein calculating the acceleration attribute value of each acceleration data segment also comprises:
    calculating the maximum amplitude value deviating from the baseline in the deceleration data segment, according to the starting point, destination point and duration of each deceleration data segment; and
    determining whether the uterine contraction data are collected at the same time; if the uterine contraction data are not collected, the type of the acceleration is not determined; if the uterine contraction data are collected, it is determined whether the starting point of the acceleration is bigger than that of the uterine contraction and whether the destination point of the acceleration is smaller than that of the uterine contraction at the same time; if the above two conditions are met, the acceleration is determined to be periodic acceleration; otherwise, it is determined to be non-periodic acceleration.

12. The method for enhancing the accuracy of recognizing fetal heart rate data acceleration according to claim 5, wherein outputting the acceleration data segment and calculation results further comprises: displaying and/or printing and/or storing and/or recognizing the acceleration data segment and the calculation results of the attribute values.

13. The method for enhancing the accuracy of recognizing fetal heart rate data acceleration according to claim 5, wherein the pre-configured acceleration determination criteria further comprises:
    firstly, the fetal heart rate data segment to be analyzed shall all be above the fetal heart rate baseline;
    secondly, the time, during which the amplitude deviating from the baseline exceeds A0, shall be equal to or bigger than T0;
    thirdly, the maximum amplitude deviating from the baseline shall be equal to or bigger than A1; and
    fourthly, the energy of the fetal heart rate data segment to be analyzed shall be equal to or bigger than P0; wherein the energy is in direct proportion to the square of the amplitude and time and may be obtained through a numerical integration method; if all of the abovementioned conditions are met, it may be determined that the fetal heart rate data segment to be analyzed is an acceleration data segment, wherein A0, T0, A1 and P0 are pre-configured parameters.

* * * * *